(12) United States Patent
Sai et al.

(10) Patent No.: US 8,703,505 B2
(45) Date of Patent: Apr. 22, 2014

(54) OPTICAL FIBER PROBE

(71) Applicant: Indian Institute of Technology Bombay, Powai (IN)

(72) Inventors: Vemulakonda Venkata Raghavendra Sai, Chennai (IN); Soumyo Mukherji, Kolkata (IN); Tapanendu Kundu, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 0 days.

(21) Appl. No.: 13/932,711

(22) Filed: Jul. 1, 2013

(65) Prior Publication Data

US 2014/0017809 A1 Jan. 16, 2014

Related U.S. Application Data

(62) Division of application No. 12/708,953, filed on Feb. 19, 2010, now Pat. No. 8,476,007.

(51) Int. Cl.
*G01N 33/551* (2006.01)
*G01N 33/543* (2006.01)

(52) U.S. Cl.
CPC ....... *G01N 33/54373* (2013.01); *Y10S 436/805* (2013.01)
USPC ............ 436/524; 436/525; 436/527; 436/805

(58) Field of Classification Search
None
See application file for complete search history.

(56) References Cited

U.S. PATENT DOCUMENTS

| 7,511,820 B2 | 3/2009 | Chau et al. |
| 2007/0109544 A1 | 5/2007 | Chau et al. |
| 2007/0109545 A1 | 5/2007 | Chau et al. |
| 2008/0203281 A1 | 8/2008 | Sanders et al. |

OTHER PUBLICATIONS

Bar et al., Dendrimer-Modified Silicon Oxide Surfaces as Platforms for the Deposition of Gold and Silver Colloid1 Monolayers: Preparation Method, Characterization, and Correlation between Microstructure and Optical Properties, Langmuir 1996,12, pp. 1172-1179.

Chau et al., Fiber-optic Chemical and Biochemical Probes Based on Localized Surface Plasmon Resonance, Sensors and Actuators B 113, 2006, pp. 100-105.

Cooper, Optical Biosensors: Where Next and How Soon?, Drug Discovery Today, Dec. 2006, vol. 11, Nos. 23/24, pp. 1061-1067.

Endo et al., Label-free Detection of Peptide Nucleic Acid-DNA Hybridization Using Localized Surface Plasmon Resonance Based Optical Biosensor, Analytical Chemistry, Nov. 1, 2005, vol. 77, No. 21, pp. 6976-6984.

Englebienne, Use of Colloidal Gold Surface Plasmon Resonance Peak Shift to Infer Affinity Constants from the Interactions Between Protein Antigens and Antibodies Specific for Single or Multiple Epitopes, Analyst, Jul. 1998, vol. 123, pp. 1599-1603.

Frederix et al., Biosensing Based on Light Absorption of Nanoscaled Gold and Silver Particles, Analylical Chemistry, Dec. 15, 2003, vol. 75, No. 24, pp. 6894-6900.

Grabar et al., Preparation and Characterization of Au Colloid Monolayers, Analytical Chemistry, Feb. 15, 1995, vol. 67, No. 4, pp. 735-743.

(Continued)

*Primary Examiner* — Chris L Chin

(74) *Attorney, Agent, or Firm* — Foley & Lardner LLP

(57) ABSTRACT

A biosensor having an optical fiber having at least one curved portion configured to enhance penetration of evanescent waves; and one or more nanoparticles associated with the optical fiber, and configured to enhance localized surface plasmon resonance.

3 Claims, 11 Drawing Sheets

(56) References Cited

OTHER PUBLICATIONS

Gupta et al., Fibre-optic Evanescent Field Absorption Sensor Based on a U-shaped Probe, Optical and Quantum Electronics 28, 1996, pp. 1629-1639.

Homola et al., Surface Plasmon Resonance (SPR) Sensors, Springer Series on Chemical Sensors and Biosensors, 2006, No. 4, pp. 45-67.

Homola et al., Surface Plasmon Resonance Sensors for detection of Chemical and Biological Species, Chemical Reviews, 2008, No. 1 08, pp. 462-493.

Jain et al., Review of Some Interesting Surface Plasmon Resonance-enhanced Properties of Noble Metal Nanoparticles and Their Applications to Biosystems, Plasmonics, 2007, No. 2, pp. 107-118.

Jensen et al., Electrodynamics of Noble Metal Nanoparticles and Nanoparticle Clusters, Journal of Cluster Science, 1999, vol. 10, No. 2, pp. 295-317.

Khijwania et al., Fiber Optic Evanescent Field Absorption Sensor with High Sensitivity and Linear Dynamic Range, Optics Communications 152, Jul. 1, 1998, pp. 259-262.

Khijwania et al., Maximum Achievable Sensitivity of the Fiber Optic Evanescent Field Absorption Sensor Based on the U-shaped Probe, Optics Communications 175, Feb. 15, 2000, pp. 135-137.

Kim et al., Label-Free DNA Biosensor Based on Localized Surface Plasmon Resonance Coupled with Interferometry, Analytical Chemistry, Mar. 1, 2007, vol. 79, No. 5, pp. 1855-1864.

Leung et al., A Review of Fiber-optic Biosensors, Sensors and Actuators B 125, Mar. 15, 2007, pp. 688-703.

Lin et al., Detection of Phosphopeptides by Localized Surface Plasma Resonance of Titania-Coated Gold Nanoparticles Immobilized on Glass Substrates, Analylical Chemistry, Oct. 1, 2006, vol. 78, No. 19, pp. 6873-6878.

Littlejohn et al., Bent Silica Fiber Evanescent Absorption Sensors for Near-Infrared Spectroscopy, Applied Spectroscopy, 1999, vol. 53, No. 7, pp. 845-849.

Mitsui et al., Optical Fiber Affinity Biosensor Based on Localized Surface Plasmon Resonance, Applied Physics Letters, Nov. 1, 2004, vol. 85, No. 18.

Muskens et al., Quantitative Absorption Spectroscopy of a Single Gold Nanorod, Journal of Physical Chemistry C, 2008, No. 112, pp. 8917-8921.

Nath et al., A Colorimetric Gold Nanoparticle Sensor to Interrogate Biomolecular Interactions in Real Time on a Surface, Analylical Chemistry, Feb. 1, 2002, vol. 74, No. 3, pp. 504-509.

Nath et al., Label-Free Biosensing by Surface Plasmon Resonance of Nanoparticles on Glass: Optimization of Nanoparticle Size, Analytical Chemistry, Sep. 15, 2004, vol. 76, No. 18, pp. 5370-5378.

Nehl et al., Optical Properties of Star-Shaped Gold Nanoparticles, Nano Letters, Mar. 28, 2006, vol. 6, No. 4, pp. 683-688.

Okamoto et al., Local Plasmon Sensor with Gold Colloid Monolayers Deposited upon Glass Substrates, Optics Letters, Mar. 15, 2000, vol. 25, No. 6, pp. 372-374.

Prasad et al., A Capacitive Immunosensor Measurement System with a Lock-in Amplifier and Potentiostatic Control by Software, Meas. Sci. Technol. 10, 1999, pp. 1097-1104.

Ruddy et al., Evanescent Wave Absorption Spectroscopy Using Multinode Fibers, Journal of Applied Physics, May 15, 1990, vol. 67, No. 10, pp. 6070-6074.

Sai, V.V. et al., "Novel U-bent fiber optic probe for localized surface plasmon resonance based biosensor," Biosensor & Bioelectronics, vol. 24, Issue 9, pp. 2804-2809, May 15, 2009.

Slavik et al., Ultrahigh Resolution Long Range Surface Plasmon-based Sensor, Letter to the Editor, Sensors and Actuators B 123, 2007, pp. 10-12.

Su et al., Interparticle Coupling Effects on Plasmon Resonances of Nanogold Particles, Nano Letters, 2003, vol. 3, No. 8, pp. 1087-1090.

Tang et al., Fiber-optic Biochemical Sensing with a Colloidal Gold-modified Long Period Fiber Grating, Sensors and Actuators B 119, Jan. 18, 2006, pp. 105-109.

Turkevich et al., A Study of the Nucleation and Growth Processes in the Synthesis of Colloidal Gold, Discussions of Faraday Society 11,1951, pp. 55-75.

US Notice of Allowance on U.S. Appl. No. 12/708,953 DTD Mar. 1, 2013.

US Office Action on U.S. Appl. No. 12/708,953 DTD Oct. 25, 2012.

Wang et al., Nanorice: A Hybrid Plasmonic Nanostructure, Nano Letters, 2006, vol. 6, No. 4, pp. 827-832.

Wei et al., Sensitive Plasmonic Biosensor Using Gold Nanoparticles on a Nano Fiber Tip, Plasmonics in Biology and Medicine III, Proceedings of SPIE, 2006, vol. 6099.

OPTICAL FIBER PROBE

CROSS-REFERENCE TO RELATED APPLICATIONS

This application claims a priority benefit, under 35 U.S.C. §121, as a divisional application of U.S. patent application Ser. No. 12/708,953, filed Feb. 19, 2010. The above-identified application is hereby incorporated by reference herein in its entirety.

BACKGROUND

Biosensors are becoming more and more popular in the market these days. Optical biosensors are used by analysts and chemists for their ease of operation and compatibility with other types of measurement techniques such as gravimetric and calorimetric techniques. Various attempts have been made to improve the sensitivity and the accuracy of optical biosensors.

SUMMARY

An embodiment herein relate to a sensor comprising an optical fiber having a probe region having at least one curved portion configured to enhance penetration of evanescent waves; and one or more nanoparticles associated with the probe region, and configured to enhance localized surface plasmon resonance. In one aspect, the sensor further comprises an optical setup configured to detect absorbance of radiation in the probe region. In another aspect, at least a part of the probe region comprises a receptor that is configured to bind to an analyte in a sample. In another aspect, the probe region is configured for exposure to a sample. In another aspect, at least a part of the curved portion is substantially U or V shaped.

In another aspect, at least a part of the probe region further comprises at least a first substantially straight portion that is configured for exposure to a sample and a second substantially straight portion that is configured to avoid exposure to the sample. In another aspect, a part of the substantially straight portion has the nanoparticles thereon. In another aspect, the optical setup comprises a radiation source at one end of the probe and a detector at the other end of the probe. In another aspect, the sensor further comprises a flow cell configured to contain a sample and to surround at least a part of the curved portion.

In another aspect, the flow cell has a volume of greater than zero microliter and less than 100 microliter. In another aspect, the sensor is configured to detect immobilization of bioreceptors and/or immunocomplex formation. In another aspect, the sensor is configured to detect a presence of an analyte in the sample and to detect a concentration of the analyte in the sample. In another aspect, the nanoparticles comprise a metal exhibiting the surface plasmon resonance.

Another embodiment relates to a method comprising bending an optical fiber to form a bent optical fiber having a curved portion; and coating nanoparticles on at least a portion of the bent optical fiber to form a probe region. In one aspect, the method further comprises connecting an optical setup configured to detect a difference in refractive index of a sample and a reference material, wherein the optical setup is configured to further detect absorbance of radiation in the bent optical fiber. In another aspect, the optical setup comprises a radiation source connected to one end of the bent optical fiber and a spectrophotometer at the other end of the bent optical fiber. In another aspect, the method further comprises coating at least a part of the probe region with a receptor that binds to an analyte in the sample.

Another embodiment relates to a method comprising exposing a sample to a bent optical fiber having a curved portion and detecting a difference in refractive index of the sample and a reference material. In one aspect, the method, further comprises detecting a presence of an analyte in the sample and detecting a concentration of the analyte in the sample. In another aspect, the analyte comprises a biological molecule or a non-biological molecule.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
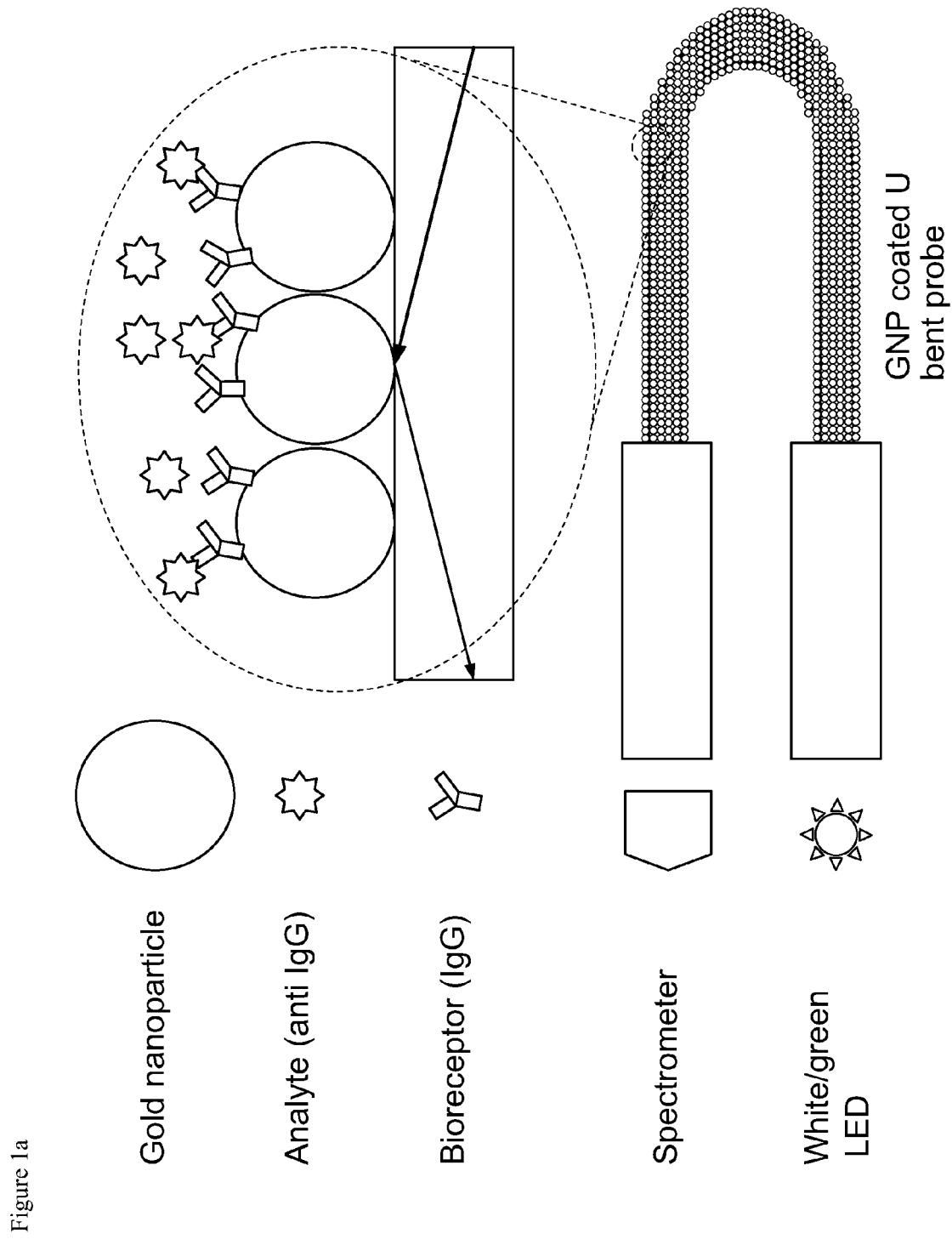
FIG. 1a shows an illustrative embodiment of an optical set-up and sensing scheme used for experiments with U-bent fiber optic probe.

The embodiments relate to a bent optical fiber sensor, e.g., a biosensor, having a nanoparticle coating, in which the sensitivity and the resolution of detection are increased. The embodiments relate to a sensor comprising an optical fiber having at least one curved portion configured to enhance penetration of evanescent waves; and one or more nanoparticles associated with the optical fiber, and configured to enhance localized surface plasmon resonance. The embodiments relate to a method including bending an optical fiber to form a bent optical fiber having a curved portion and coating nanoparticles on at least a portion of the bent optical fiber. The embodiments also relate to a method comprising exposing a sample to a bent optical fiber having at least one curved portion and detecting a difference in refractive index between the sample and a reference material.

The reference material typically is a solution of known concentration of a material suspected of being in the sample. Indeed, several solutions of the reference material may be prepared at different known concentrations. In this manner, a calibration curve for a particular material may be generated. The concentration of the sample can be determined by comparison with the calibration curve. Differences as little as $1/1000$ of a refractive index may be detected.

The term "optical fiber or fiber optic" refers to a wire that can transfer light from one end to other by internal reflection of light within the fiber. An optical fiber may be cladded or uncladded. Cladded optical fibers generally have a structure from the center to the periphery including core, cladding, and buffer. An uncladded optical fiber, lacking cladding, generally has an exposed core.

The core can be made of any transparent material such as silica (glass) or a polymer that transmits light. In cladded fiber optics, the core is typically surrounded by, but not limited to, a thin plastic or silica cladding that helps transmit light through the optical fiber with minimum loss. The cladding may be covered with a tough resin buffer layer. Both the core and the cladding may be made of dielectric materials such as, but not limited to, doped silica glass and polymers. To confine the optical signal in the core, the refractive index of the core is typically greater than that of the cladding. The typical values of the refractive index for the cladding and the core of an optical fiber are 1.46 and 1.48, respectively. The boundary between the core and cladding may either be abrupt, in step-index fiber, or gradual, in graded-index fiber. The radius of the optical fiber (core plus cladding) can be from about 0.1 mm to about 2 mm, for example about 0.2 mm to about 0.5 mm.

In an embodiment herein, the optical fiber has a core diameter of about 0.2 mm and a cladding thickness of zero, as the optical fiber was an uncladded optical fiber. In another embodiment, the optical fiber includes a core and a cladding, however the cladding is partially removed. That is, the cladding is removed over a portion of the optical fiber, the remaining fiber maintaining its cladding.

The term "evanescent waves" in the context of the optics used in the embodiments herein refer to waves that are formed at the core/cladding interface as the light passing through the fiber core undergoes total internal reflection at its boundary when the angle of incidence of light at the interface is above the so-called critical angle. At the point of reflection, a small amount of light at the interface of core/cladding can be experienced as an electric field into the cladding and exponentially reduces within a distance of $\lambda/10$ (typically less than 50 nm) from the core/cladding interface. This electric field is called an evanescent field or evanescent wave (EW).

Cladding material (either polymer or silica) is generally removed in order to access these evanescent waves. The cladding material may be removed, for example, by using a sharp surgical blade, a file, sand paper, or any other abrasive tool. When a molecule is bound, for example by functionalizing with amino, to an uncladded portion of the optical fiber (i.e., where clad polymer has been removed or is absent allowing to access to the core), the optical absorbance properties of the molecule can be monitored by the light passing through the optical fiber as explained in more detail below. This is called evanescent wave absorbance phenomenon. Evanescent waves can be used to illuminate very small objects stained associated with fluorophores such as biological cells for microscopy (as in the total internal reflection fluorescence microscope). Evanescent waves can also be used to detect immobilization of bioreceptors and immunocomplex formation during analyte binding on the surface of gold nanoparticles coated on an optical fiber.

Surface plasmons, also known as surface plasmon polaritons, are surface electromagnetic waves that propagate in a direction substantially parallel to an interface of two materials, e.g., at the interface of a vacuum or material with a positive dielectric constant, and a negative dielectric constant (usually a metal or doped dielectric). Since the wave is on the boundary, e.g., of the metal and the external medium (air or water for example), these oscillations can be very sensitive to any change of this boundary, such as the adsorption of molecules to the metal surface. Surface plasmon resonance occurs when surface plasmons are excited in a resonant manner using, for example, an electron or light beam (visible and/or infrared, for example) and matching the impulse of the beam and the surface plasmons. Surface plasmons can be used to enhance the surface sensitivity of several spectroscopic measurements including fluorescence, Raman scattering, and second harmonic generation. Surface plasmon resonance reflectivity measurements, as discussed in more detail below, can be used to detect molecular adsorption, such as polymers, DNA or proteins, etc.

Localized surface plasmon resonance is a surface phenomenon occurring at the surface of a noble (defined below) metal nanoparticle. The valency band electrons absorb energy at a particular wavelength of radiation to become free electrons in the conduction band. The free electrons or plasmons give rise to resonance when metal nanoparticles (MNPs) such as, but not limited to, gold nanoparticles (GNPs) are excited at a wavelength that depends on size and material of the nanoparticle. As a result, a strong electric field is developed at the surface of the GNP (also known as evanescent field). According Maxwell's equations, this electric field is influenced by the dielectric constant of the surrounding environment of the GNP. When the dielectric constant changes, e.g., due to change in refractive index, absorption at a wavelength or the peak absorption (excitation) wavelength also changes.

The term "nanoparticle" refers to a particle having at least one dimension sized between 1 and 1000 nanometers. The nanoparticle can comprise a noble-metal containing nanoparticle. "Noble metal" refers to the metals of groups 9, 10 and 11 of transition metal series in the periodic table (of the IUPAC style). The noble metal of the noble-metal containing nanoparticle includes one or more of rhodium, iridium, palladium, silver, osmium, iridium, platinum, gold or combinations thereof. In alternative embodiments, the nanoparticle is not a noble metal. Any material which exhibits surface plasmon resonance may be used. Other materials include, but are not limited to, copper and aluminum.

Nanoparticles of noble metals such as gold and silver are known to exhibit optical absorption and scattering properties in UV (approximately 10-380 nm)-Visible (approximately 380-760 nm)-near IR region (Approximately (760-2,500 nm) termed as localized surface plasmon resonance (LSPR). The extinction band due to LSPR can be influenced by the size, shape and composition of nanoparticles and most importantly by the surrounding environment. Refractive index changes taking place at the surface of the nanoparticles result in changes in absorbance and a red-shift in absorbance peak ($\lambda_{max}$). These properties may be exploited, for example, in implementing colorimetric biosensors.

The term "biosensor" refers to a device for the detection of an analyte that combines a biological component with a detector component such as but not limited to, physicochemical, electrochemical, photometric, and piexoelectric. A biosensor is generally an analytical device having a biological recognition element (e.g., an enzyme, receptor, DNA, antibody, or microorganism) operatively connect with an electrochemical, optical, thermal, or acoustic signal detector such that together they permit analyses of properties or quantities such as, but not limited to, chemical, electrical, magnetic, physical, biological, and optical. Generally, the biosensor has at least three parts: (1) A sensitive biological element such as a biological material (e.g., tissue, microorganisms, organelles, cell receptors, enzymes, antibodies, or nucleic acids), a biologically derived material or biomimic. The sensitive element can be created by biological engineering. (2) A transducer or a detector element that transforms the signal resulting from the interaction of an analyte with the biological element into another signal that can be measured and quantified. The analyte may be any substance or chemical constituent that can be determined in an analytical procedure. Analytes include, but are not limited to ligands, nucleic acids, proteins, and enzymes. The transducer or detector element could be a physicochemical, optical, piezoelectric, electrochemical or magnetic element among others. (3) Associated electronics or signal processors generally for the display or transmission of the results.

An example of a biosensor is the blood glucose biosensor, which uses the enzyme glucose oxidase to break blood glucose down. In doing so it first oxidizes glucose and uses two electrons to reduce FAD (a component of the enzyme glucose) to FADH2, which in turn is oxidized by the electrode (accepting two electrons from the electrode) in a number of steps. The resulting current is a measure of the concentration of glucose. In this case, the electrode is the transducer and the enzyme is the biologically active component. Another example of biosensor includes arrays of many different detector molecules. Biosensor applications may use organisms which respond to toxic substances to warn us of their presence.

The LSPR properties of gold and silver nanoparticles can be utilized in liquid phase as well as in monolayers coated on glass/quartz substrates, for example, to develop colorimetric biosensors. One embodiment may include gold capped silica/polystyrene nanoparticle coated substrates. Other embodiments may include nanoparticles of rhodium, iridium, palladium, silver, osmium, iridium, platinum, or combinations thereof. The absorbance response of MNPs-based sensors can be further enhanced by coating MNPs on an efficient absorbance based sensor, such as a siloxane polymer. Optical fiber probes can be used to enhance the sensitivity of the LSPR-based biosensor by using a fiber optic evanescent-wave sensing scheme. MNP coated on uncladded straight fiber probes can be used for chemical and biochemical sensing. In an alternative embodiment, the MNPs may be coated on a bent optical fiber.

Evanescent wave based absorbance sensitivity of bare (unclad, uncoated surface of fiber core) fiber optic probes can be increased by modifying the probe geometry. Different fiber optic probe designs including straight, U-bent, tapered tip, and biconical tapers can be employed in development of absorbance based bio/chemical sensors. Some embodiments relate to U-bent probes having one or more of (and not limited to) good sensitivity, compactness, ease in fabrication, and possibly higher compatibility with instrument configurations. Evanescent fields around U-bent probes are stronger than in a straight probe.

Although not intending to be bound by a particular theory, the increased field may be due to the creation of higher order modes from lower order modes concentrated along the centre of optical axis of a bent fiber. It results in a significant increase in penetration depth of the evanescent field at the bent region and beyond in the direction of light propagation. This gives U-bent probes a higher sensitivity in absorbance measurements. U-bent probes have been demonstrated to have a 10 fold improvement in absorbance sensitivity over straight probes (Gupta, B. D., Dodeja, H., Tomar, A. K., 1996. Optical and Quantum Electronics 28, 1629-1639.) and verified by embodiments herein, for example, in the case of the 0.2 mm fiber core diameter.

In the embodiments herein, addition of the metal (gold) nanoparticles on the probe surface increases absorbance sensitivity substantially by taking advantage of the phenomenon of LSPR occurring on such nanoparticles and by exciting such LSPR using the enhanced evanescent field from the bent probes (FIG. 1a). Both U-bent probe and MNP contribute to the sensitivity. U-bent probe facilitates better excitation of MNP. With MNP coating, the sensitivity of a U-bent probe is several times, e.g., 2-10 times more, than a similar uncoated U-bent probe.

Figure 1B:
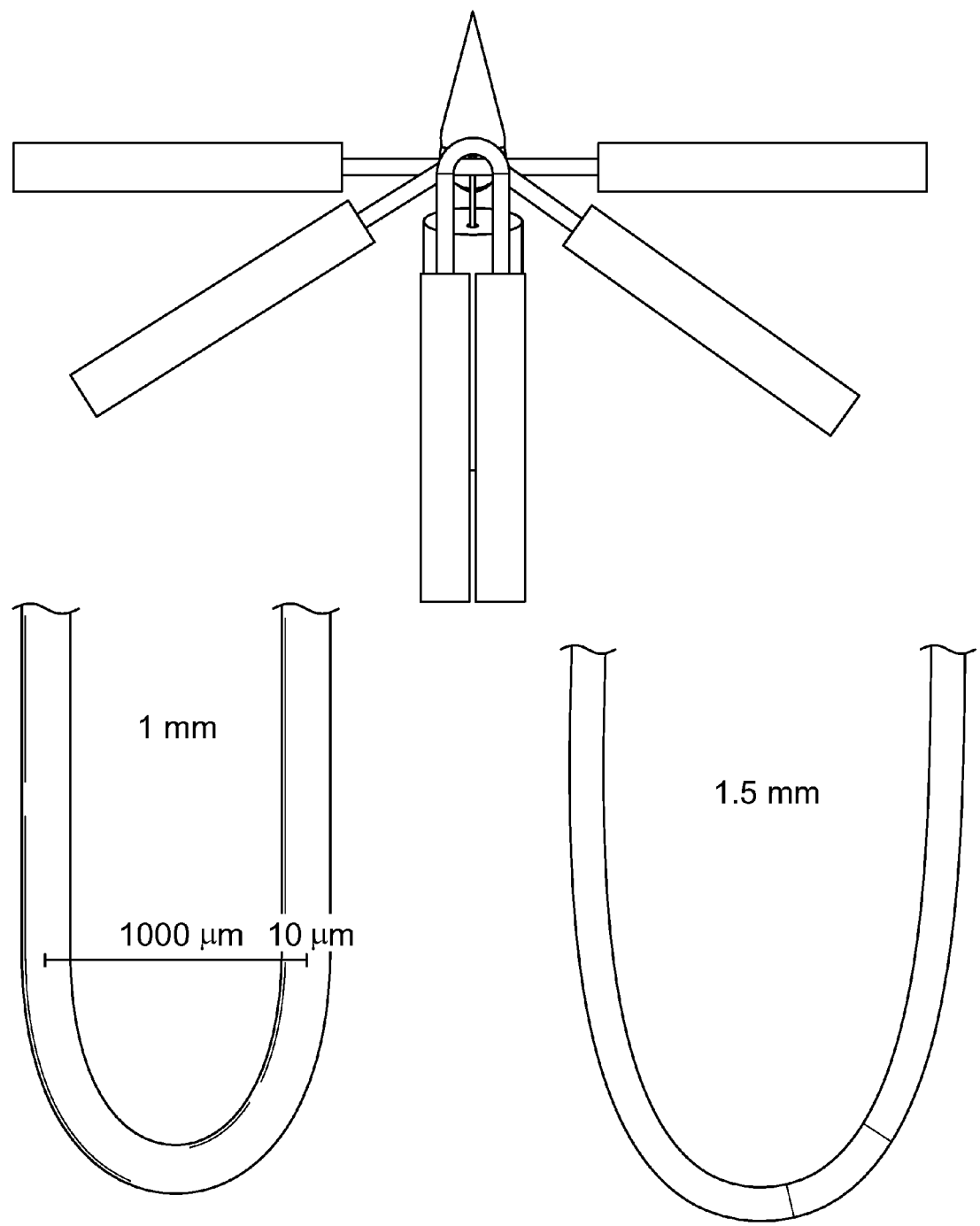
FIG. 1b shows an illustrative embodiment of the fabrication of U-bend fiber optic probes using candle flame; images of bent probes of different bend diameters were taken using an optical microscope under 25× magnification.

The embodiments herein relate to novel LSPR biosensors using MNP coated U-bent fiber optic probes, having a high sensitivity obtained by coating MNP on the U-bent fiber probe. The embodiments relate to a procedure to fabricate U-bend probes from uncladded straight fibers (FIG. 1b). For example, the complete optical set-up may include one or more of, but is not limited to, a fiber probe, a light emitting diode (LED) and a detector that operates in the visible, IR, or UV range, along with signal conditioning and processing electronics. A spectrometer (spectrophotometer, spectrograph, spectroscope, or other suitable device) can be used for analyzing the output obtained from the fiber probes (FIG.

1c). Additionally, an optical detector sensitive at a particular LSPR frequency may be used.

The term "analyte" refers to a substance or chemical constituent that is determined in an analytical procedure. For instance, in an immunoassay, the analyte may be the ligand or the binder, while in blood glucose testing, the analyte is glucose. In medicine, analyte often refers to the type of test being run on a patient, as the test is usually determining the presence/absence and/or quantity/percent of a chemical or biological substance in the human body. Often, an analyte (in clinical chemistry may be referred to as component) itself cannot be measured, but a measurable property of the analyte can. For instance, one cannot measure glucose but can measure the glucose concentration. In this example, "glucose" is the component and "concentration" is the kind-of-property. In laboratory and layman jargon the "property" is often left out provided the omission does not lead to an ambiguity of what property is measured.

The term "sensitivity" refers to the change in absorbance as a result of a change in refractive index unit due to analyte binding. For example, in an embodiment, a U-bent probe of 200 μm diameter with a bend radius of 0.75 mm gave rise to a sensitivity of 35 ΔA/RIU at 540 nm.

The term "resolution" refers to the smallest refractive index change that the sensor is able to measure. The resolution of the sensor probe in the embodiment above was $3.8 \times 10^{-5}$ RIU.

The term "probe" or "probe region" refers to the MNP coated portion of the optical fiber sensor. Typically, the probe region is the uncladded exposed fiber core with MNP coating on the uncladded exposed fiber core. Typically, the complete probe region or a portion of the probe region comes in contact with the sample analyte.

The term "penetration depth" refers to the distance away from optical fiber core at which electric field experienced at the surface of the core reduces by 70.7%.

Although the length of biosensor probe and the resolution of a biosensor are directly proportional, the length of the probe cannot be increased beyond a certain limit as the sample analyte volume required also increases. The biosensors of the embodiments herein, however, have increased sensitivity and could be configured for use with low sample volume of 100 microliters or less. However, if a larger or wider flowcell is used, a larger sample volume can be accommodated. Indeed, the biosensor can be used without a flow cell—the biosensor can work in any body of analyte, for example, a beaker, cup, glass, pond or river. The embodiments herein satisfy the need for a biosensor with increased sensitivity and/or resolution.

The embodiments relate to a U-bend shaped fiber optic based biosensor having improved sensitivity, which depends on the bend diameter and the length of the uncladded optical fiber after the bent region for a given radius of the fiber core. As shown in FIG. 1a, the bend in fiber forces the light travelling along the centre (optical axis) of fiber to come to periphery and increases penetration of waves into samples. Among the embodiments herein, the U-bent shaped fiber optic includes a straight optical fiber (0.2 mm of core diameter) bent in to a substantially U shape, typically bent 180 degrees. The bend, however, may be less than 180 degrees or greater than 180 degrees. In an embodiment, the bend may vary from 90 degrees to 270 degrees. In another embodiment, the bend may vary from 1 degree to 359 degrees. In another embodiment, the "U" shape has flat bottom. That is, the U is made of three straight line segments. In still another embodiment, the optical fiber has substantially a V shape.

Among the embodiments of the biosensors, the features include a U-bent optical fiber probe and a nanoparticle layer on the U-bent optical fiber probe. The nanoparticle layer could be a metal nanoparticle (MNP) monolayer over the probe surface. The MNP could be a gold nanoparticle (GNP). In the probe region of the optical fiber biosensor of the embodiments herein, the plastic cladding can be removed to expose fiber core and a MNP monolayer can be deposited, as discussed in more detail below, on the core of the optical fiber.

In the embodiments, the U-bent fiber probe could be made by obtaining an optical fiber having a core and a cladding, with the core having a given fiber core diameter. The optical fiber is cut into a desired length. Then a length in the middle of the fiber (that is, a portion not including one of the ends) is uncladded to expose the core. For example, the buffer and cladding could be stripped by using a sharp surgical blade, a file, sand paper, or any other abrasive tool. Optionally, the terminal ends of optical fiber could be polished to reduce light loss due to coupling. Polishing may be accomplished by using emery papers with lower roughness in sequential order or with a polishing machine, for example. The optical fibers are bent after applying heat to soften the optical fibers using a flame, a laser, or any other suitable heat source. The optical fibers are bent to obtain a certain bend radii, for example, as small as 0.5 mm with satisfactory repeatability as shown in FIG. 1b. Optical fibers may be bent to have bend radii, for example, between 0.5 mm and 1.75 mm. In an alternative embodiment, a fiber is cast with a U shape.

For fabricating different bend radii, different portions of the flame could be used. For example, the bluish flame at the bottom of the flame could be used to obtain smaller radius, e.g., 0.5-0.75 mm. The region at the tip of the flame could be used for larger radius, e.g., 1 mm and above (FIG. 1b). That is, in general, the smaller the desired radius, the hotter the flame is used.

Fiber probes may be functionalized, for example, with amino silane to bind the MNP to the sensor surfaces. In some embodiments, the uncladded optical fiber in the probe region may be treated with sulphochromic solution for a few minutes, and then washed twice in de-ionized DI water to create (additional) silanol sites (Si—OH) on the surface of the core in the probe region for covalent binding of aminosilane molecules. Fiber probes could then be dehydrated at higher than 100° C. for a few hours, dipped in silane solution prepared in an appropriate solvent for a few minutes in an oxygen free environment such an argon-containing environment. The probe region could then be washed in absolute ethanol after the silane treatment and condensed by heating at greater than 100° C. for several minutes.

Gold nanoparticles could then be bound to amine functionalized U-bent fiber probe region. The silanized U-bent probe could be positioned with the bend region of probe in a custom-made L-shaped glass capillary. The capillary tube could used to incubate the probe region with MNP solution (see example below).

A spectrometer (spectrophotometer, spectrograph, spectroscope, or other suitable device) may be used to measure the absorbance of light passing through the optical fiber to detect a change in refractive index of the surrounding environment of the biosensor due to a target analyte binding to the MNP bound to the probe, and thereby measures the concentration of the target analyte. The concentration may be determined, for example, from the following equation:

$$A = k \cdot \frac{\sqrt{2} \cdot 4\lambda}{3 \cdot 2\pi \cdot r \cdot NA} \cdot \varepsilon_{ex} CL$$

Where 'r' is the radius of the optical fiber into which light is coupled, 'NA' is the numerical aperture at the sensing region of the fiber, 'λ' is the wavelength of light, '$\varepsilon_{ex}$' is the extinction coefficient of absorbing medium (GNP), and C is the concentration of absorbent molecules bound per unit circumferential surface area of the fiber.

The working of the biosensor of the embodiments herein could be based on the exploitation of localized surface plasmon resonance (LSPR) properties of MNP bound to the surface of the core of a U-bent optical fiber and detection of optical absorbance properties of MNP using enhanced evanescent wave absorbance (EWA) phenomenon taking place at U-bent region of fiber.

The U-bent geometry improves penetration of evanescent waves at the probe region. The U-bent geometry is not limited to just a U-bent geometry of the optical fiber but any bent fiber optic probe that is bent to give better sensitivity. The U-bent radius value depends on the radius of the optical fiber (0.2 mm core diameter in an embodiment herein). The effective probe lengths can be typically 1 cm (2 cm of uncladded probe bent into U shape at the centre such that each straight portion of the U shape is about 1 cm). The typical angle formed between the straight portions at the U-bend is about 180°. As discussed above, however, the angle may vary between 90 degrees to 270 degrees. In another embodiment, the angle may vary from 1 degree to 359 degrees. Optionally, there can be multiple bends or coiled fibers as the probe region.

An U-bend improves the penetration of the EW, which helps in bringing the entire volume of the MNP under the influence of the EW. The embodiments relate to a U-bent shaped fiber optic based biosensor based on detection of absorbance changes that could be obtained due to refractive changes caused by analyte binding at the surface of MNP.

Figure 2A:
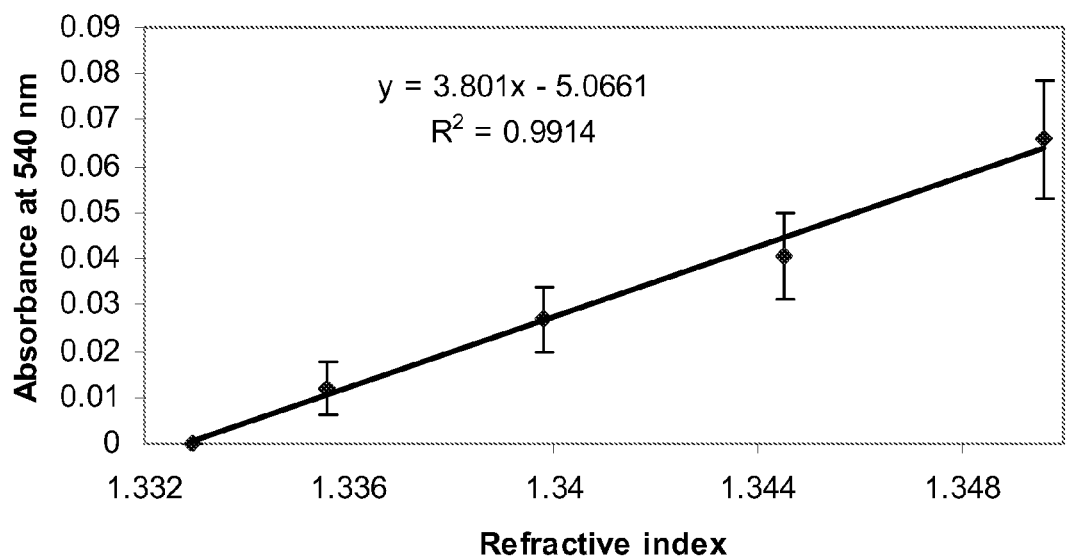
FIG. 2a shows an illustrative embodiment of absorbance changes at 540 nm obtained with MNP coated straight fiber probes of 2 cm probe length and 200 µm core diameter for sucrose solutions of different refractive indices. The sensitivity of these probes was 3.8 $A_{540\,nm}$/RIU.
Figure 2B:
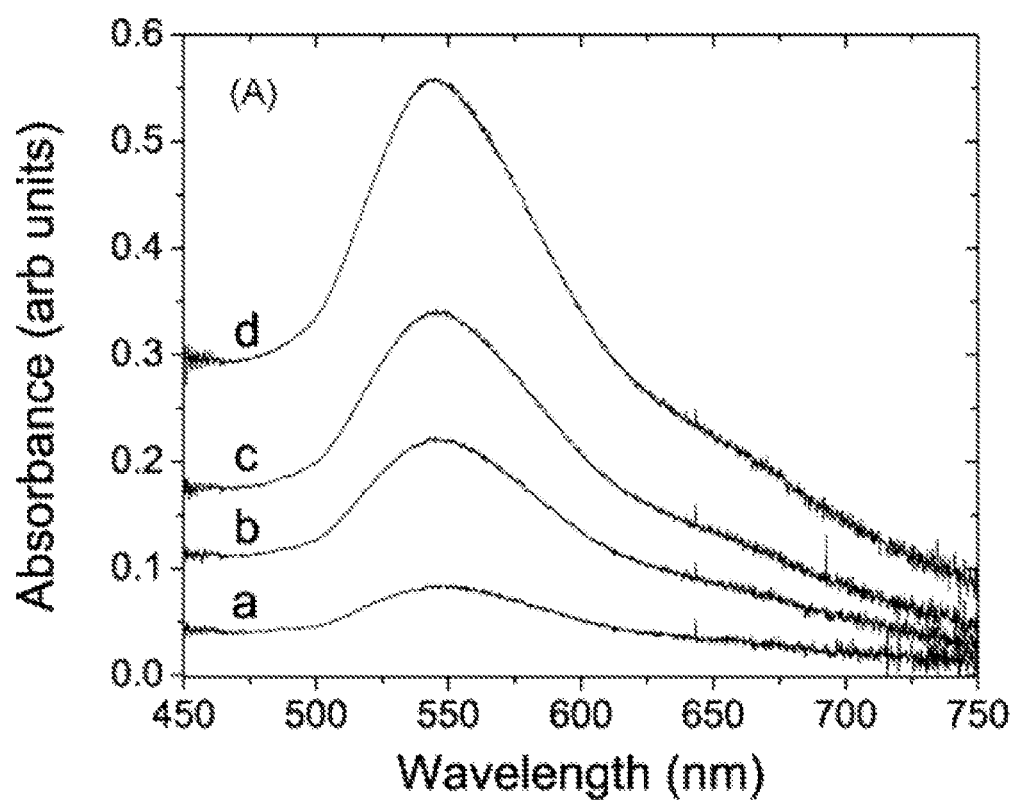
FIG. 2b shows an illustrative embodiment of absorbance spectra obtained for sucrose solutions with refractive index values (a) 1.3359, (b) 1.3403 (c) 1.3433 (d) 1.3494.
Figure 2C:
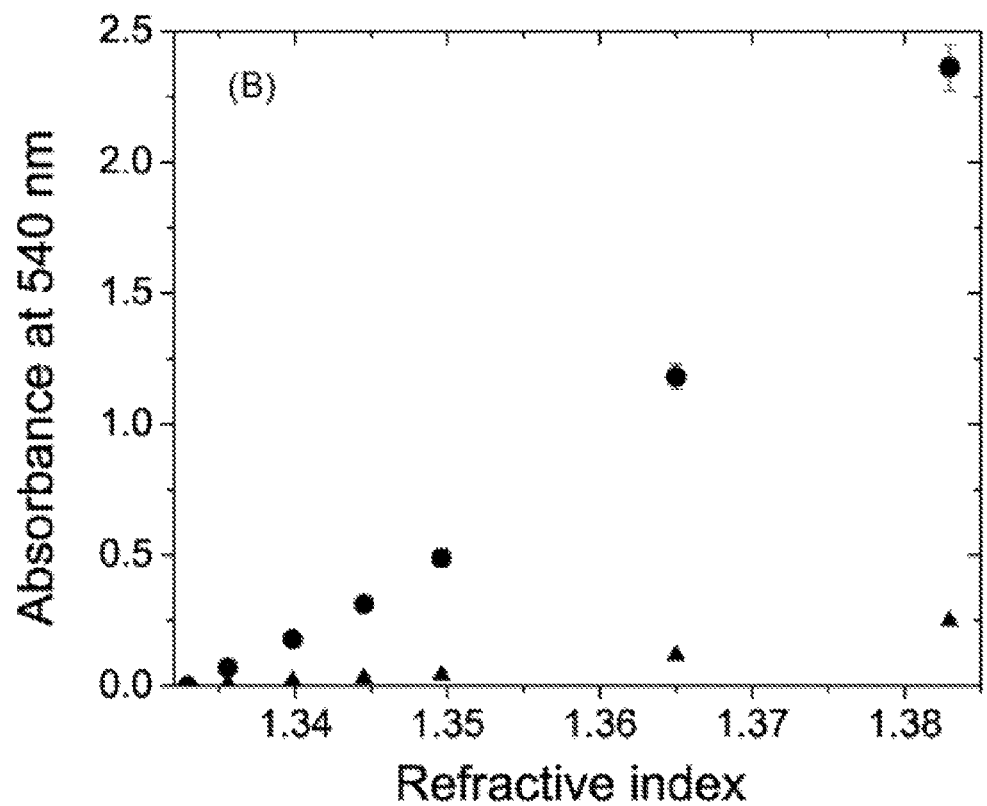
FIG. 2c shows an illustrative embodiment of absorbance response obtained from bare (▲) and GNP coated (●) U-bend probes of 0.5 mm radii in presence of media of different refractive indices ranging from 1.33 to 1.38.
Figure 2D:
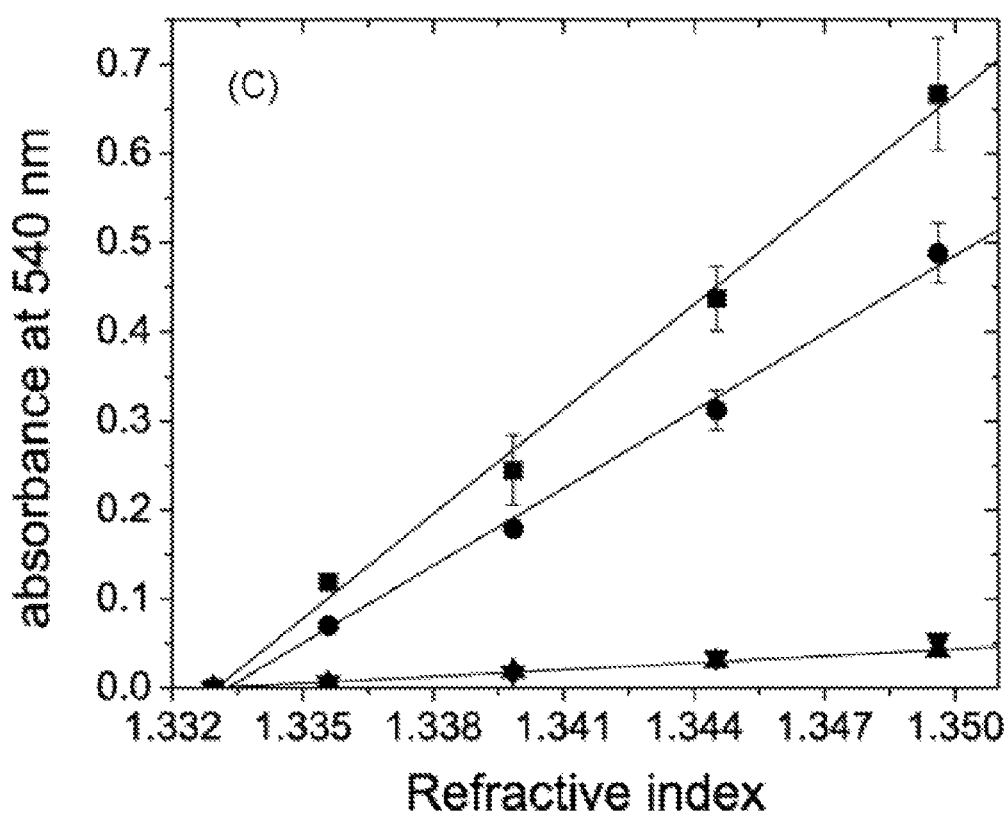
FIG. 2d shows an illustrative embodiment of sensitivity of GNP bound U-bent probes of radii 0.5 mm (●) and 0.75 (■) mm and the corresponding bare probes 0.5 mm (▲) and 0.75 mm (▼) to RI changes at the probe surface between 1.33 and 1.35. A linear fit for the absorbance responses obtained for the two probes resulted in a slope or sensitivity 28.98 and 35.19 with $R^2$ equal to 0.9979 and 0.9976 respectively. A linear fit for bare probes gave a sensitivity of 2.55 with $R^2$ equal to 0.9986 (n=3).

For example, absorbance sensitivity of these probes to refractive index changes at the surface of MNP could be determined by subjecting the probes to sucrose solutions of different concentrations. The absorbance spectra after subjecting the GNP coated probe to consecutively higher % (w/w) sucrose solutions with RI varying from 1.33 to 1.35 could be recorded by using a spectrometer (FIG. 2b). The optical fiber probe of embodiments herein could be sensitive to a wide range of refractive index changes between 1 (air) to 1.38 (FIG. 2c). A significant (3.8 $A_{540\,nm}$/RIU) rise in absorbance could be obtained for different RI solutions compared to MNP coated straight probes (FIG. 2a). The absorbance change due to a change in refractive index at the surface of MNP could be measured at a particular wavelength using a detector or spectrometer (FIG. 2d).

Figure 3:
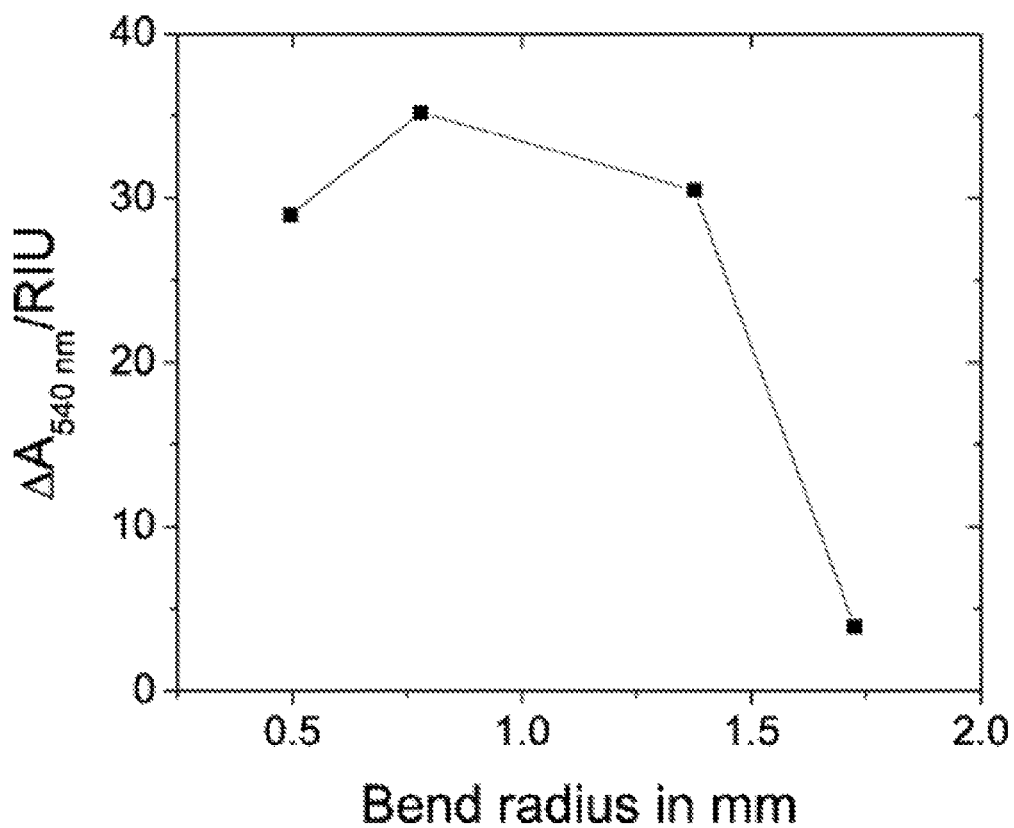
FIG. 3 shows an illustrative embodiment of dependence of sensitivity (AA/RIU) of U-bent probes on bend diameter. Absorbance changes were measured from U bent probes of different diameters by subjecting them to various % (w/w) sucrose solutions and slope of the linear fit was taken as the sensitivity of the probes.

A maximum possible sensitivity of the U-bent probes could be optimized by modifying the bend radius. U-bent probes with different radii give rise to different sensitivity. For example, fiber optic probes with core diameter of 0.2 mm could result in highest possible sensitivity for a U-bend radius of 0.75 mm (FIG. 3). U-bend probes give rise to improved sensitivity compared to that of straight probes as the probes are bent to obtain reduced bend radius. An increase in the RI sensitivity could be observed as the bend radius reaches an optimum value, where conversion of additional number of lower order modes to higher order modes with increasing bend radius. A further reduction in the bend radius to obtain least possible bend radius causes reduction in sensitivity due to higher optical losses at the bend region.

The refractive index changes as a result of the analyte binding to a receptor on the surface of MNP coated probe can also be monitored efficiently by the embodiments of the biosensor. This leads to better absorbance of light in the optical fiber probe and therefore better measurement of refractive index of the surrounding medium. Thereby, the biosensor can be used to detect several biological and non-biological molecules of interest. A biological molecule is one that is either present in blood stream or can be extracted from biological cells, or blood, plasma, urine, contaminated water, etc. For biological molecules, the probe can be coated with a specific bioreceptor depending on the bioreceptor-analyte pair. Non-biological molecule can be a molecule of interest in environmental monitoring, e.g., pesticide. For non-biological molecules, the probe can be coated with specific receptors for non biological molecules.

EXAMPLES

Reagents and Materials

Tetra chloro aurate ($HAuCl_4$), Cystamine (HS—$C_2H_4$—$NH_2$), Phosphate buffer saline (PBS) were obtained from Sigma. Aminosilane (N-[3-trimethoxy silyl]propyl)ethylene diamine, >99%) was procured from Aldrich. Glutaraldehyde (OHC—$C_2H_4$—CHO) was obtained from Fluka. Trisodium citrate and acetic acid were purchased from SD fine chemicals, India. All antibodies, human IgG (HIgG), rabbit IgG (RIgG) and goat anti-human IgG—affinity purified (Ga-HIgG) and bovine serum albumin (BSA) were obtained from Bangalore Genei, India. All the reagents were of analytical grade. All solutions were prepared using de-ionized (DI) water obtained from a MilliQ filtration system. Optical fibers of diameter 200 μm and NA=0.37, obtained from Thorlabs®.

Synthesis of Gold Nanoparticles

Gold nanoparticles used in these experiments were synthesized as follows: 50 mM $HAuCl_4.3H_2O$ in DI water was prepared as a stock solution. 0.2 mL of 50 mM gold chloride solution was added to 39.15 mL of DI water and heated until it began to boil. 0.647 mL of 5 mg/ml sodium citrate trihydrate solution was added as soon as boiling commenced. Heating was continued until the solution turned pale purple in color. Then the solution was removed from the hot plate and allowed to cool to room temperature. The molar ratio of citrate to gold was 1.1. The average size of the synthesized nanoparticles was 40 nm. The absorbance peak for gold nanoparticles solution was at 530 nm as shown in FIG. 1d by the grey curve.

Fiber Probe Preparation

The optical fibers of core fiber diameter of 200 μm were cut into 40 cm long pieces. A 2 cm length in the middle of the fiber was decladded to expose its core. The buffer and cladding were stripped by using a sharp surgical blade. The terminal ends of optical fiber were polished by using emery papers with 5, 1 and 0.3 μm roughness in sequential order. The optical fibers were bent using a wax candle flame to obtain bend radii as small as 0.5 mm with satisfactory repeatability (FIG. 1b).

For fabricating different bend radii, different portions of the flame. The bluish flame at the bottom of the flame was used to obtain radius of 0.5-0.75 mm. The region at the tip of the flame was used for radius of 1 mm and above.

The bent portions were observed under an optical microscope and diameters were measured from the images of U-bent probes by using Axiovision® software (Carl-Zeiss®). The core diameter of the fiber was found to be uniform at the bent portion.

Functionalization of Fiber Probes

Fiber probes were functionalized with amino silane to bind the gold nanoparticles to the sensor surfaces. Substrates were treated in sulphochromic solution (100 ml of conc. $H_2SO_4$ added to 500 μg of $K_2Cr_2O_7$ in 1 ml of DI water) for 8-10 minutes thoroughly and then washed twice in DI water. This creates (additional) silanol sites (Si—OH) on the surface for covalent binding of aminosilane molecules. Fiber probes were dehydrated at 115° C. for 2 hours. They were then dipped in 1% Silane prepared in ethanol: acetic acid (10:4) solvent for 3-5 minutes in Argon ambient. Acetic acid helps in restricting the formation of multilayers of silane that could lead to aggregation of gold nanoparticles on sensor surfaces. Substrates were washed in absolute ethanol after silane treatment and condensed by heating at 110° C. for 20 minutes.

Optical Set-Up

Figure 1C:
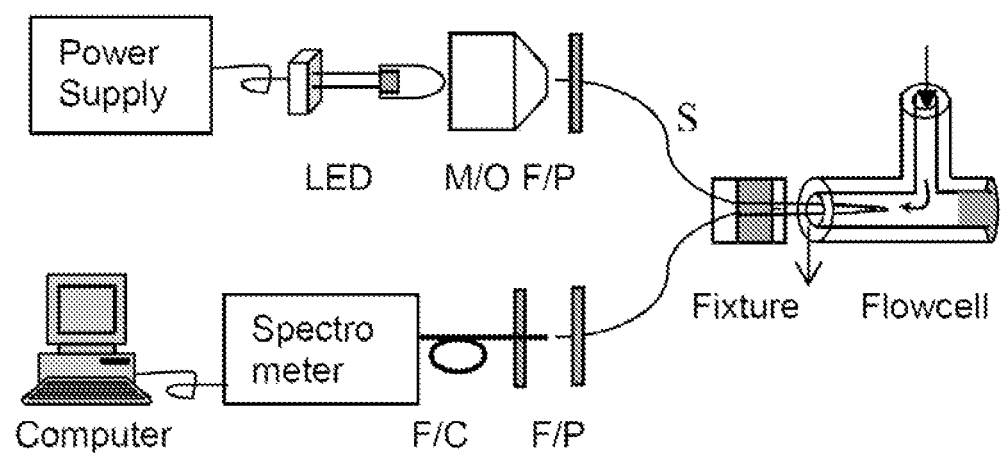
FIG. 1c shows an illustrative embodiment of an experimental set-up along with capillary flow cell for fluid interactions with the probe. Probe was fixed to a glass slide and decladded portion was introduced into flow cell. Flow cell was a custom-made T shaped glass capillary tube of 2.5 mm diameter with one end closed as shown in FIG. 1c. Liquid was introduced into capillary using 1 ml syringe from the top and collected from the other end. M/O: microscope objective; F/P: fiber positioner; F/C: connectorized fiber; S: sensor (i.e., probe).
Figure 1D:
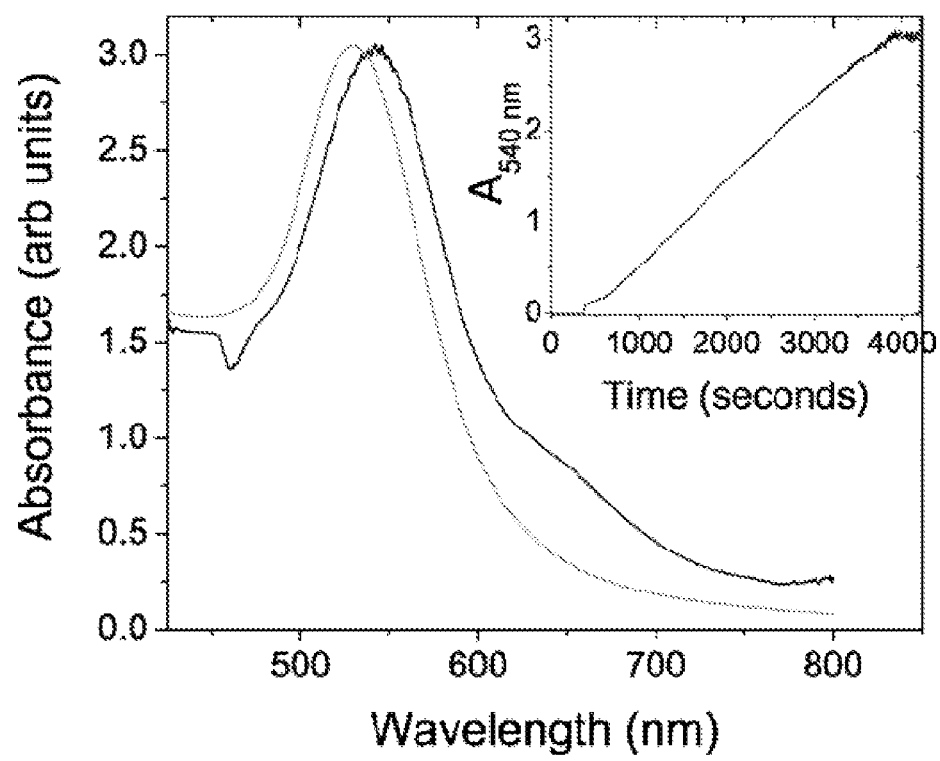
FIG. 1d shows an illustrative embodiment of absorbance spectrum obtained from a fiber probe having bound gold nanoparticle (GNP) (black) and the GNP solution (gray); Inset: real-time response observed at 540 nm due to gold nanoparticles bound to the fiber probe of bend radius 0.75 mm.

The optical set-up for absorbance measurements has a white light emitting diode (5W4HCA-H20-ULTRA, 19.0-25.0 cd at 20 mA, view angle 20°, 5 mm clear epoxy from Roithner LaserTechnik, Austria) with spectral emission between 430-700 nm and a fiber optic spectrometer (FIG. 1c). One of the polished ends of prepared fiber probe was held by a fiber chuck in fiber coupler (Newport®, USA). Light from LED was focused through a microscopic objective lens, 40×, 0.6 NA, onto the fiber end. The decladded fiber sensor portion was held within a custom-made glass capillary channel with inlet and outlet ports. The other end of the probe was held by using a fiber positioner. Light from this end was collected into a fiber optic spectrometer (USB 4000, Ocean Optics®). A schematic giving the details of experimental set-up is shown in FIG. 1c. Binding events taking place on fiber probe surface were monitored as absorbance changes at 540 nm in real-time and the full absorbance spectra were recorded at the end of the experiments. Signal-to-noise ratio (SNR) was improved by averaging 100 consecutive spectra. Spectrasuite® software was used to acquire absorbance spectra and real time absorbance changes at a particular wavelength.

Formation of GNP SAMs on Fiber Probes

Gold nanoparticles were bound to amine functionalized U-bent fiber probes as described below. A silanized U-bent probe with bend radius of 0.75 mm was positioned between the source and detector with bend region of probe in a custom-made L-shaped glass capillary of 2.5 mm diameter. The capillary tube was used to incubate the probe with GNP solution and also to subject the probes to solutions with different refractive indices at later stages of the experiments.

The GNP solution was introduced into the capillary and absorbance spectrum was monitored in real-time. A linear increase in absorbance at 540 nm was observed as shown in FIG. 1d (inset). The peak absorbance of spectrum reached nearly three units within a time span of 30-60 minutes of incubation. Above an absorbance of about 2.5 to 3 units, the high absorption of light at the peak absorption wavelength of GNP led to a low SNR, which coupled to the spectral characteristics of the commercial LED used in these experiments, gave rise to a noisy signal. After one hour of incubation, fiber probes were washed with DI water. The absorbance spectrum recorded from the probe was as shown in FIG. 1d.

The spectral characteristics of GNP coated fibers were slightly different from that of GNP in solution phase. A red shift in the peak wavelength and a broadening of spectrum was noticed in the spectrum. Further a plateau centered at 650 nm was observed in the spectrum. The red shift in the peak wavelength was observed from the beginning of the deposition of GNP onto the probe. An average red shift of 13.4±1.4 nm was observed. The occurrence of red shift is likely due to plasmon coupling between the chemisorbed GNP with the interparticle distance less than ~2.5 times the particle size. Hence, the cause for red shift in the spectrum can be attributed to plasmon coupling between the nanoparticles resulting from high surface density. The plateau, observed at 650 nm in addition to the red shift, may have resulted from aggregation of GNP due to higher surface roughness of aminosilane layer on fiber and/or the size distribution of nanoparticles.

An embodiment was to investigate the effectiveness of the GNP coated probes in detection of refractive index changes in the bulk as well microenvironment around the fiber probe by means of measurement of absorbance changes.

Absorbance Sensitivity to Refractive Index Changes

Subsequently, GNP coated probes were used for testing the bulk refractive index sensitivity. Since the spectral range of interest is around 540 nm, a light source restricted in the spectral range might be sufficient to achieve desired sensitivity in measuring refractive indices. In order to achieve higher SNR, a high intensity, commercially available green LED (peak: 525 nm; FWHM: 50 nm) was used as the light source. The integration time was also increased to aid in this effort. Sucrose solutions of different concentrations with refractive index between 1.33 and 1.40 were introduced and absorbance response was recorded. FIG. 2b shows the absorbance spectra obtained by subjecting the GNP coated probe with consecutively higher % (w/w) sucrose solutions with RI varying from 1.33 to 1.35. A significant rise in absorbance was obtained for different RI solutions. However, no significant shift in peak wavelength was observed.

Bare U-bent probes are sensitive to refractive index. In order to investigate the contribution of bending alone in the absorbance response, a bare bent probe of 0.5 mm radii and later the same probe coated with GNP were subjected to RI variation between 1.33 and 1.40 and absorbance response at 540 nm was monitored. The bare probe was found to induce a change in absorbance that is approximately one tenth of the absorbance obtained in presence of GNP monolayer. This trend was observed for entire range of refractive indices as shown in FIG. 2c. An important observation was the limitation of range of the RI detection between 1.33 and 1.38 RIU in aqueous phase. Effective light coupling between U-bent probe and GNP as well as significant absorption of light in presence of high RI solutions led to peak absorbance values of more than 2.5 units for RI of above 1.38. This resulted in poor signal to noise ratio in the output as <0.001% of the light launched from an LED into the probe is transmitted to the detector end.

U-bent probes with radii 0.5 mm and 0.75 mm were coated with gold nanoparticles and tested with sucrose solutions to obtain information about sensitivity and resolution of probes for refractive index measurements. Sensitivity, defined as the ratio of the change in absorbance to the change in RI, was found to be linear between 1.33 and 1.35 RIU as shown in FIG. 2d. Sensitivity was found to be influenced by the bend radius of the probe with its value of 28.98 and 35.19 $\Delta A_{540\ nm}$/RIU for 0.5 mm and 0.75 mm probes respectively.

Effect of Bend Radius on Sensitivity

The sensitivity of the U-bent probes may be improved by exploring its optimum bend radius. Hence, U-bent probes with different radii were fabricated and their RI sensitivity was investigated. Results obtained in this study are shown in FIG. 3. An increase in the RI sensitivity was observed as the bend radius was reduced from 1.7 mm to 0.75 mm. This rise in sensitivity may be attributed to conversion of additional number of lower order modes to higher order modes with increasing bend radius. However, for the bend radius below 0.75 mm, sensitivity reduced due to higher losses at the bend region. The sensitivity of the probes of 1.7 mm radius was an order lower than that of 0.75 mm and similar to that of 2 cm long GNP coated straight probes (FIG. 2a). Hence, U-shaped bending of fiber probes may be effective for bend radii below 1.7 mm.

Biosensor Applications

Figure 4:
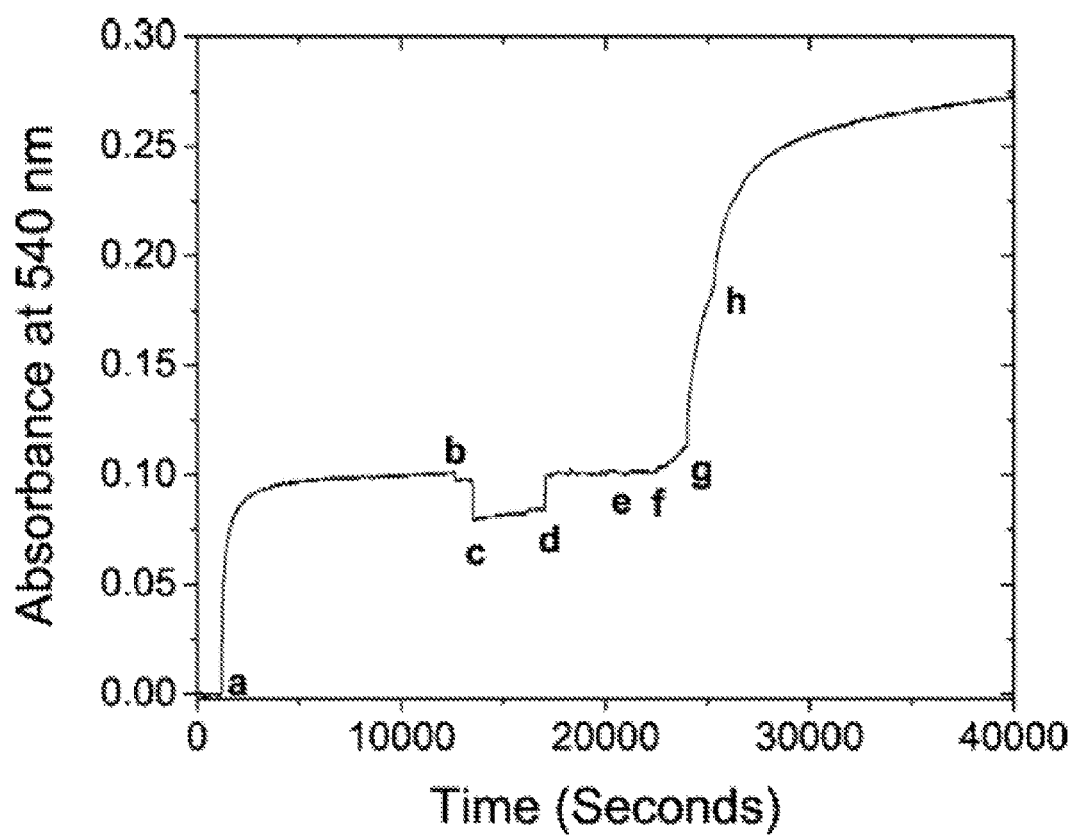
FIG. 4 shows an illustrative embodiment of real time changes in absorbance recorded from a GNP coated U-bent fiber probe of 0.5 mm bend radius during binding of IgG-anti IgG. (a) Aldehyde functionalized GNP coated probe was incubated with 0.1 mg/ml of Human IgG (HIgG); (b) washed with PBS; (c) incubated with 2 mg/ml BSA in PBS and (d) finally washed with PBS. HIgG immobilized probes were subjected to goat anti human IgG (GaHIgG) concentrations of (e) 0.06 µg/ml; (f) 0.6 µg/ml; (g) 6 µg/ml for 20 minutes followed by (h) 30 µg/ml until saturation.

Immobilization of bioreceptors and immunocomplex formation during analyte binding on the surface of gold nanoparticles leads to increase in effective refractive index of the microenvironment. It results in increase in the optical absorbance of the gold nanoparticles. The ability of GNP coated U-bent probes in detecting these absorbance changes was tested by using IgG—anti IgG as bioreceptor—analyte pair. In order to minimize the probe-to-probe variation in the sensor response, U-bent probes of 0.5 mm bend radii were used in these studies due to their repeatability in the fabrication. U-bent fiber probes were silanized and incubated in gold nanoparticle solution and washed with DI water after 45 minutes. Gold nanoparticles were functionalized by incubating the probes in 5 mM cystamine prepared in absolute ethanol for 60 minutes, followed by 1% glutaraldehyde solution in water for 30 minutes. Human immunoglobulin G (HIgG) was immobilized on the functionalized probes by dipping in 0.1 mg/ml of HIgG in PBS for 4 hours. HIgG Immobilized probes were treated with 2 mg/ml BSA to reduce non-specific binding followed by incubation with $F_c$ specific goat anti-human IgG (GaHIgG). Interestingly, a downward shift in the peak absorbance was recorded during the incubation of probes in BSA solution. This was attributed to the difference in the refractive index values of PBS and BSA. PBS and 2 mg/ml BSA solution prepared PBS were experimentally found to have refractive index values of 1.3347 and 1.3331 respectively at 589.3 nm (measurements carried out with Pulfrich refractometer). Due to the sensitivity of GNP coated U-bent probe to bulk refractive index changes, the change in refractive index of the medium might have been caused a shift in the absorbance value. The drop in the absorbance value was found to be in the order of the theoretical value obtained from multiplication of RI sensitivity of the probe and difference in the refractive index values of PBS and BSA. Absorbance change at 540 nm due to binding of HIgG and BSA was found to be 0.1±0.006 and 0.005±0.001 respectively (FIG. 4). The saturated absorbance response due to binding of GaHIgG to immobilized HIgG was 0.15±0.02.

Figure 5:
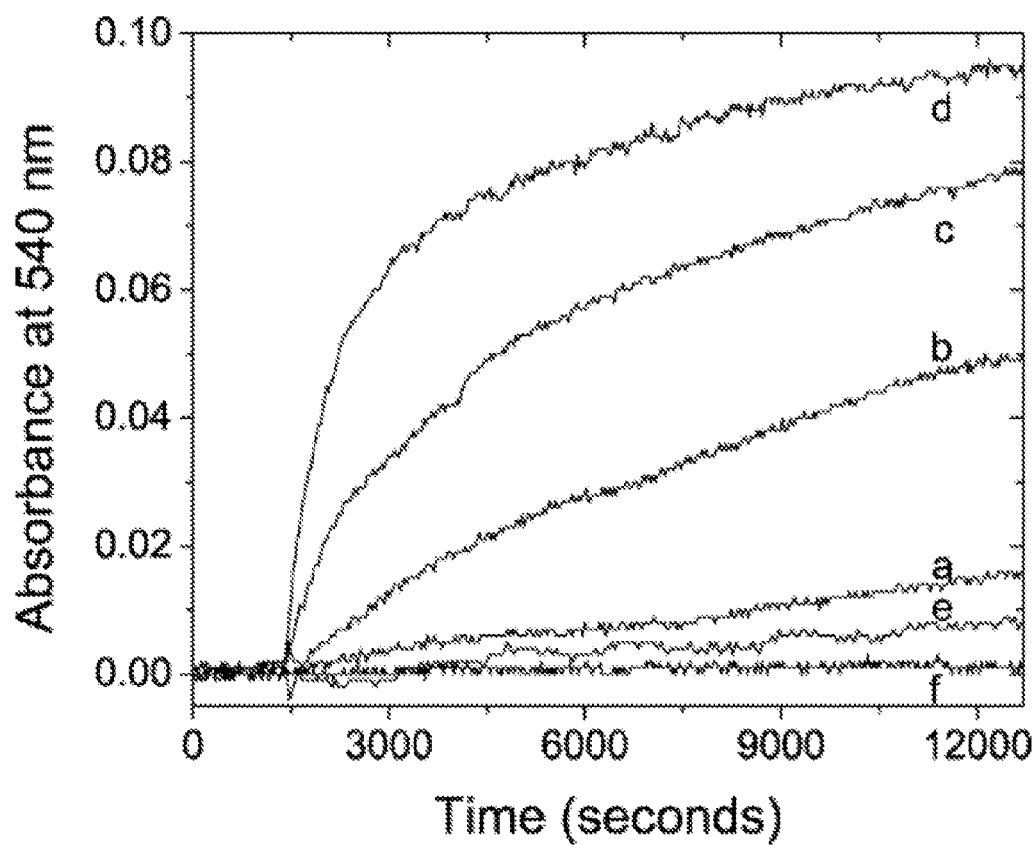
FIG. 5 shows an illustrative embodiment of absorbance changes monitored at 540 nm caused by binding of anti-human IgG to human IgG immobilized GNP coated U-bent fiber probes of 0.5 mm bend radii for (a) 0.12 µg/ml, (b) 0.6 µg/ml, (c) 6 µg/ml and (d) 15 µg/ml of goat anti-human IgG. (e) Absorbance due to non-specific binding of anti human IgG to rabbit IgG immobilized probe. (f) Baseline response of HIgG immobilized probe observed for 3 hours in presence of PBS.

HIgG immobilized probes were tested with different concentrations of GaHIgG ranging between 0.1 µg/ml and 15 µg/ml. The absorbance response was observed for 3 hours to test the ability of the probes for real-time continuous monitoring. The real time absorbance changes at 540 nm from different probes were as shown in FIG. 5. It is important to note that saturated or steady state response was not obtained before of 3 hours of incubation. In another study, a similar steady rise in the absorbance for lower analyte concentrations has been observed throughout the detection span (Nath and Chilkoti 2004). Saturation or steady state response depends on the availability of free binding sites and/or analyte molecules to the probe. The response obtained in this study probably indicates that a larger number of binding sites are available on the probe surface compared to the analyte molecules available to bind to them. A slow rate of diffusion through a comparatively large analyte space may also contribute to the slow increase after the initial rise. To test the non-specific binding, probe was immobilized with rabbit IgG. Absorbance response was monitored in presence of 6 µg/ml of goat anti-human IgG. The rise in absorbance due to non-specific binding was found be less than half that of specific binding of 0.12 µg/ml of goat anti-human IgG. Hence, U-bent probes of 0.5 mm bent radius were capable of detecting a concentration of 0.12 µg/ml (0.8 nM) of the analyte.

The sensitivity obtained using GNP coated U-bent probes was 30 times better than that of nanoSPR sensors consisting of GNP coated cover glass substrates reported by Nath, N. and Chilkoti A., 2004. Analytical Chemistry 76, 5370-5378. The resolution of probes were calculated as $3.8\times10^{-5}$ RIU and $5.2\times10^{-5}$ RIU for 0.75 mm and 0.5 mm probes respectively (assuming an ability to detect 0.0015 abs units). The improved resolution using the bent probes was 15 times that of LSPR based 400 µm diameter, 5 cm long straight fiber optic biochemical probes and similar that of distal end sensor configuration with 50 µm core fiber reported by Chau, L-K., Lin, Y-F., Cheng, S-F., Lin, T-J., 2006. Sensors and Actuators B 113, 100-105.

Using a 200 µm core diameter bent optical fiber, the overall and effective probe lengths in this study were 2 and 1 cm respectively.

Apart from gold nanoparticles, a high RI sensitivity may be obtained by incorporating gold colloids with higher extinction coefficient such as nanostars, nanorice and nanorods on U-bent probes. Similar to nanospheres, absorption/scattering spectrum of the other gold colloids can be fine-tuned by varying the aspect ratio. In addition, the extinction properties of these gold colloids in near infrared (NIR) region also may aid in enhancement in the sensor response due to the dependence of evanescent wave absorbance on the wavelength of operation.

The use of novel U-bent fiber optic probes for absorbance based LSPR sensor applications was demonstrated as being capable of detecting bulk refractive index changes with a sensitivity and resolution of 35.19 $A_{540\,nm}$/RIU and $3.8\times10^{-5}$ RIU respectively. The results obtained in case of biosensor applications had a minimum detection limit of 0.8 nM of anti-IgG. Compared to conventional SPR sensors, the preparation of these probes is far simpler, easily executable in ordinary laboratory conditions and less expensive.

In the detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method comprising:
a.) providing a sensor comprising:
an optical fiber having a probe region having at least one curved portion configured to enhance penetration of evanescent waves; and
one or more nanoparticles in optical communication with the probe region, and configured to enhance localized surface plasmon resonance,
wherein at least a part of the probe region further comprises at least a first substantially straight portion, coated with nanoparticles, configured for exposure to a sample and a second substantially straight portion configured to avoid exposure to the sample, and
wherein the at least one curved portion comprises a coiled fiber; and
b.) exposing a sample to the curved portion of said sensor and detecting a difference in refractive index of the sample and a reference material.

2. The method of claim 1, further comprising detecting a presence of an analyte in the sample and detecting a concentration of the analyte in the sample by said detected difference in refractive index.

3. The method of claim 2, wherein the analyte comprises a biological molecule or a non-biological molecule.

* * * * *

UNITED STATES PATENT AND TRADEMARK OFFICE
CERTIFICATE OF CORRECTION

PATENT NO. : 8,703,505 B2  
APPLICATION NO. : 13/932711  
DATED : April 22, 2014  
INVENTOR(S) : Sai et al.

It is certified that error appears in the above-identified patent and that said Letters Patent is hereby corrected as shown below:

In the Specification

In Column 5, Line 36, delete "piexoelectric." and insert -- piezoelectric. --, therefor.

In Column 10, Line 25, delete ">99%)" and insert -- >99% --, therefor.

Signed and Sealed this
Twenty-sixth Day of August, 2014

Michelle K. Lee
*Deputy Director of the United States Patent and Trademark Office*